(12) United States Patent
Furukawa

(10) Patent No.: US 8,551,971 B2
(45) Date of Patent: Oct. 8, 2013

(54) COMPOSITION FOR TREATMENT OF PANCREATIC CANCER

(75) Inventor: Toru Furukawa, Tokyo (JP)

(73) Assignee: Tokyo Women's Medical University, Tokyo (JP)

( * ) Notice: Subject to any disclaimer, the term of this patent is extended or adjusted under 35 U.S.C. 154(b) by 0 days.

(21) Appl. No.: 13/499,005

(22) PCT Filed: Sep. 13, 2010

(86) PCT No.: PCT/JP2010/065744
§ 371 (c)(1),
(2), (4) Date: Jun. 13, 2012

(87) PCT Pub. No.: WO2011/040220
PCT Pub. Date: Apr. 7, 2011

(65) Prior Publication Data
US 2012/0252011 A1   Oct. 4, 2012

(30) Foreign Application Priority Data
Oct. 1, 2009   (JP) .................................. 2009-229503

(51) Int. Cl.
*A61K 48/00*   (2006.01)
(52) U.S. Cl.
USPC ......... 514/44; 536/24.5; 536/24.31; 536/24.1

(58) Field of Classification Search
None
See application file for complete search history.

(56) References Cited

U.S. PATENT DOCUMENTS

2008/0113351 A1 *   5/2008   Naito et al. ........................ 435/6

OTHER PUBLICATIONS

Gilmore et al. (J. Drug Targeting, 2004, vol. 12:315-340).*
International Search Report issued Nov. 30, 2010 in International (PCT) Application No. PCT/JP2010/065744.
E. Y. Ahn et al., "Disruption of the NHR4 Domain Structure in AML1-ETO Abrogates SON Binding and Promotes Leukemogenesis", Proc. Natl. Acad. Sci, vol. 105, No. 44, pp. 17103-17108, Nov. 4, 2008.
W. Greenhalf et al., "A Selection System for Human Apoptosis Inhibitors Using Yeast", Yeast, vol. 15, No. 13, pp. 1307-1321, 1999.

* cited by examiner

*Primary Examiner* — Kimberly Chong
(74) *Attorney, Agent, or Firm* — Wenderoth, Lind & Ponack, L.L.P.

(57) ABSTRACT

Disclosed is a composition for treating pancreatic cancer. The composition comprises a pharmaceutically effective amount of an antisense nucleic acid or siRNA that inhibits expression of at least one gene selected from the group consisting of SON gene, MCM5 gene, WDR5 gene, PBK gene and CENPA gene. The composition inhibits the expression of a specific gene to provide the effect of inhibiting the proliferation, survival and tumorigenicity of pancreatic cancer cells.

2 Claims, 4 Drawing Sheets

COMPOSITION FOR TREATMENT OF PANCREATIC CANCER

This application is a U.S. national stage of International Application No. PCT/JP2010/065744 filed Sep. 13, 2010.

TECHNICAL FIELD

The present invention relates to compositions for treating pancreatic cancer under the mechanism by which expression of a specific gene is inhibited.

BACKGROUND ART

A technique is known that inhibits gene expression by targeting an mRNA transcribed from the gene. RNA interference (hereinafter, also referred to as "RNAi") is a method for specifically inhibiting a gene expression by using a phenomenon in which a short complementary double-stranded RNA fragment (siRNA) promotes degradation of mRNA having the complementary sequence (Non-Patent Document 1). Antisense nucleic acid acts to form a double strand with an mRNA and inhibits the synthesis of a protein encoded by the mRNA. These techniques have made it possible to intentionally and specifically inhibit expression of any gene of a known base sequence, and revealed the usefulness of antisense nucleic acids and siRNAs as nucleic acid drugs. The synthesis methods of antisense nucleic acid and siRNA have been established, and these molecules can be produced in comparatively reasonable price.

Cancer occurs when normal cells transform into cancer cells due to functional abnormalities in molecules (nucleic acids, proteins) produced by genes. Large numbers of molecules are involved in the survival and proliferation of cancer cells, then the survival, proliferation, and tumorigenicity of cancer cells can be inhibited by finding which of these molecules have important roles, and inhibiting the expression of such important molecules. Thus, once molecules of which inhibition prevents the survival, proliferation, and tumorigenicity of cancer cells are identified, it would be possible to develop a molecular therapy targeting these molecules. further, using a specific short double-stranded RNA for the inhibition of molecule expression enables a siRNA of a specific sequence to be used as a nucleic acid drug.

It is known that pancreatic cancer is refractory worldwide. In Japan, pancreatic cancer ranks fifth as the cause of death among different organ cancers analyzed by statistics. As of year 2000, pancreatic cancer has affected 20,045 individuals, and killed 19,093. The disease is so malignant that most of the affected individuals die. The number of affected individuals is on the rise every year, tripling in the 25-year period from 1975 to 2000 (cancer statistics, Foundation for Promotion of Cancer Research).

Globally, pancreatic cancer is the fifth leading cause of death in the Western countries, and has the highest mortality among malignant tumors, with the five-year survival rate of only 4% (for example, Non-Patent Document 2). These facts indicate that it is difficult with the current medical technology to provide a cure for pancreatic cancer, and that development of an effective novel therapy is required.

Inventions are known that concern medicaments intended to treat pancreatic cancer under the mechanism by which expression of specific genes are inhibited (Patent Documents 1 and 2). However, Patent Document 1 is intended to inhibit expression of apoptosis-inhibiting genes (Bcl-2 family), and the target is not limited to pancreatic cancer. Further, only an RNA molecule needs to be accurately introduced into cancer cells in order to cause apoptosis specifically in cancer cells (i.e., not to cause normal-cell death). Patent Document 2, on the other hand, concerns CST6 gene and GABRP gene associated with pancreatic cancer. While increased expression of these genes in pancreatic cancer patients has been confirmed, it remains unconfirmed whether the increased gene expression represents a cause of pancreatic cancer. That is, while it is possible to diagnose pancreatic cancer or predict the risk of pancreatic cancer by the measurement of gene expression, it remains totally uncertain whether inhibition of gene expression has any possibility of treating pancreatic cancer.

The following information is known for SON, MCM5, WDR5, PBK and CENPA genes. SON (SON DNA binding protein) is reported as a DNA binding molecule, but detailed functions remain elusive (Non-Patent Documents 3 to 5). MCM5 (minichromosome maintenance complex component 5) is a molecule that functions as a DNA replication factor (Non-Patent Document 6). WDR5 (WD repeat domain 5) associates with histone 1-13 lysine 4, and is essential for development (Non-Patent Document 7). PBK (PDZ binding kinase) is a phosphorylating enzyme that belongs to MAP2K group, and involved in DNA damaging reaction (Non-Patent Document 8). CENPA (centromere protein A) corresponds to histone H3 that forms a chromosome centromere, and is essential for the kinetochore (Non-Patent Document 9). However, involvement of these genes in the survival, proliferation and tumorigenicity of pancreatic cancer cells is not known.

Previously, the inventor of the present application has identified a signal transduction-related gene group in pancreatic cancer cells (Non-Patent Document 10). However, a relationship between these genes and the proliferation, survival and tumorigenicity of pancreatic cancer cells is completely unknown.

Patent Document 1: JP2004-519457
Patent Document 2: JP2009-505632
Non-Patent Document 1: Fire et al. Nature 391: 806-11, 1998
Non-Patent Document 2: Zervos EE, et al. Cancer Control 11: 23-31, 2004
Non-Patent Document 3: Mattioni et al. Chromosome 101: 618-624, 1992
Non-Patent Document 4: Wynn at al. Genomics 68: 57-62, 2000
Non-Patent Document 5: Ahn at al. PNAS 105: 17103-8, 2008)
Non-Patent Document 6: Snyder at al. PNAS 102: 14539-44, 2005
Non-Patent Document 7: Wysocka at al. Cell 121: 859-72, 2005
Non-Patent Document 8: Nandi et al. Biochem Biophys Res Commun 358: 181-188, 2007
Non-Patent Document 9: McClelland at al. EMBO J 26:5033-5047, 2007
Non-Patent Document 10: Furukawa et al. Oncogene 25: 4831-9, 2006

SUMMARY OF INVENTION

Problems to be Solved by the Invention

As described above, there is a need for an effective treatment of pancreatic cancer. While the methods using antisense nucleic acid and siRNA are expected to be effective, the target genes are not fully understood. Particularly, genes concerning the proliferation, survival and tumorigenicity of pancreatic cancer cells are not known.

The present invention has been made under these circumstances, and an object is to provide a composition for treatment of pancreatic cancer of which effect is prevention of the proliferation, survival and tumorigenicity of pancreatic cancer cells due to inhibition of a specific gene expression.

Means for Solving the Problems

The inventor of the present application studied the previously identified signal transduction-related gene group in pancreatic cancer cells (Non-Patent Document 10), and examine the effect of inhibiting those genes expression on the survival, proliferation and tumorigenicity of pancreatic cancer cells in vitro and in vivo. The present invention was completed upon confirming that inhibition of specific genes expression was effective for pancreatic cancer treatment.

The invention of the present application is a composition for treatment of pancreatic cancer, which comprises a pharmaceutically effective amount of an antisense nucleic acid or siRNA inhibiting expression of at least one gene selected from the group consisting of SON gene, MCM5 gene, WDR5 gene, PBK gene and CENPA gene.

More specifically, in the composition, the sense strand of the siRNA inhibiting expression of the SON gene comprises the nucleotide sequence of SEQ ID NO: 1 or 3; the sense strand of the siRNA inhibiting expression of the MCM5 gene comprises the nucleotide sequence of SEQ ID NO: 5; the sense strand of the siRNA inhibiting expression of the WDR5 gene comprises the nucleotide sequence of SEQ ID NO: 7; the sense strand of the siRNA inhibiting expression of the PBK gene comprises the nucleotide sequence of SEQ ID NO: 9; and the sense strand of the siRNA inhibiting expression of the CENPA gene comprises the nucleotide sequence of SEQ ID NO: 11.

Further, the invention of the present application is a method for screening an active ingredient of a pancreatic cancer therapeutic agent, which comprises selecting a target substance from candidate substances that lower the expression level of at least one gene selected from the group consisting of SON gene, MCM5 gene, WDR5 gene, PBK gene and CENPA gene, or that lower the bioactivity of the protein encoded by the genes.

Effects of the Invention

The composition of the invention of the present application effectively inhibits the proliferation, survival and tumorigenicity of pancreatic cancer cells, and thus inhibits progression of pancreatic cancer or eliminates pancreatic cancer cells. The composition also can improve the prognosis of surgical operation and chemotherapy for pancreatic cancer.

Further, the screening method of the invention of the present application makes it possible to identify a low-molecular compound or the like that can be an active ingredient of a pancreatic cancer therapeutic drug.

MODE FOR CARRYING OUT THE INVENTION

Figure 1:
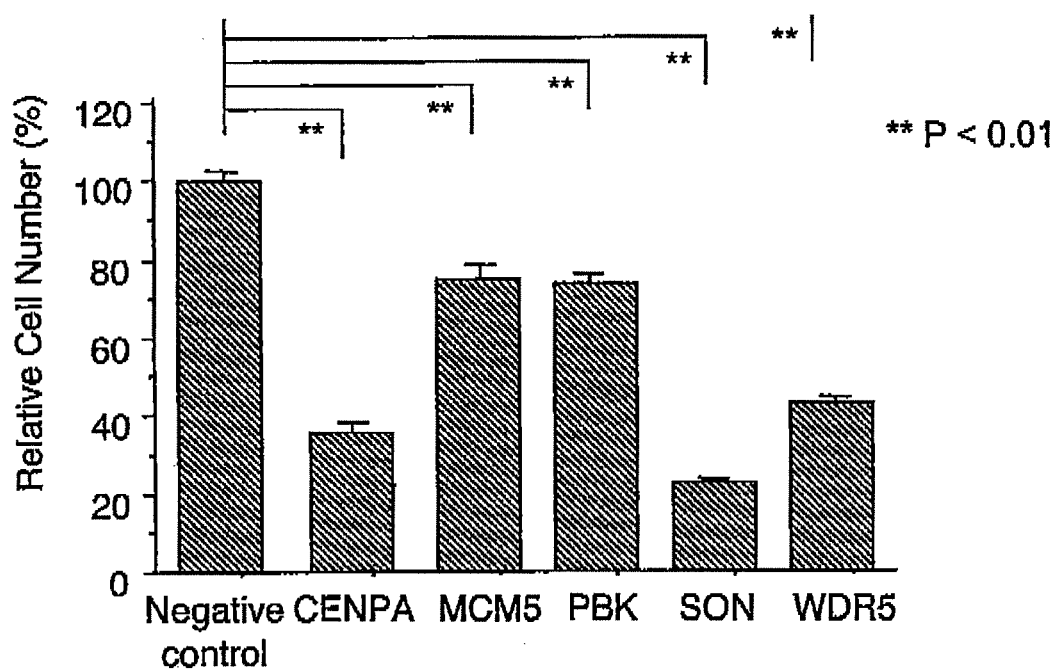
[FIG. 1] The results of examining the effect of siRNA on the proliferation of pancreatic cancer cells in Example 1.

The composition for treatment of pancreatic cancer of the present invention comprises a pharmaceutically effective amount of an antisense nucleic acid or siRNA inhibiting expression of at least one of SON gene, MCM5 gene, WDR5 gene, PBK gene and CENPA gene (hereinafter, also referred to collectively as "target genes").

The mRNA sequences of these target genes are known (SON: GenBank/NM_138927, MCM5: GenBank/NM_006739, WDR5: GenBank/NM_017588, PBK: GenBank/NM_018492, and CENPA: GenBank/NM_001809), and the antisense nucleic acid or siRNA can be prepared based on the sequence information.

The antisense nucleic acid of the present invention binds to the nucleic acid or the corresponding mRNA of the target gene to inhibit gene transcription or translation, promote degradation of the mRNA and/or inhibit expression of the protein encoded by the target gene, and finally inhibits the protein function. As long as the antisense nucleic acid can specifically hybridize with the sequence of the target gene or its mRNA (hereinafter, also referred to as "target sequence"), it may be nucleotides completely complementary to the target sequence, or nucleotides having one or more nucleotide mismatches. For example, the antisense nucleic acid of the present invention is a polynucleotide having a sequence of at least 15 contiguous nucleotides with at least 70%, preferably at least 80%, more preferably at least 90%, even more preferably at least 95% identity with the target sequence. The identity may be determined using an algorithm known in the art.

The antisense nucleic acid of the present invention may be a modified oligonucleotide. For example, the antisense nucleic acid can have nuclease resistance by using a thioated oligonucleotide.

The antisense nucleic acid of the present invention acts on the proliferation, survival and tumorigenicity of pancreatic cancer cells upon binding to the target protein-encoding DNA or its mRNA to inhibit transcription or translation, promote degradation of the mRNA, inhibit expression of the target protein, and inhibit the function of the target protein.

The composition of the present invention may be essentially the antisense nucleic acid itself, or may be prepared as various dosage forms such as a tablet, a powder, a granule, a capsule formulation, a liposome capsule, an injection, and a solution with additives such as an excipient, an isotonic agent, a solubilizer, a stabilizer, a preservative, and an analgesic added as required.

The composition containing the antisense nucleic acid of the present invention may be administered to a patient by being directly injected to the affected area, or by being injected to the blood vessel to reach the affected area. An antisense encapsulating agent may be also used to improve persistence and membrane permeation. For example, the encapsulating agent includes a liposome, poly-L-lysine, lipid, cholesterol, Lipofectin or derivatives theseof.

The dose of the antisense nucleic acid of the present invention may range from, for example, 0.1 to 100 mg/kg, preferably 0.1 to 50 mg/kg according to the pathology of the patient.

The siRNA of the present invention is a double-stranded RNA molecule that prevents translation of the target gene mRNA, and includes a sense strand and an antisense strand for the target mRNA. The siRNA may be introduced into a cell by using standard methods. For example, a method may be used that introduces an RNA template DNA molecule into a cell. Here, the sense strand and the antisense strand may have an integrated hairpin structure so that a single transcript is obtained from the DNA molecule.

In the present invention, the sense strand and the antisense strand of the siRNA preferably have nucleotide lengths of 500, 200, 100, 50, 25, or less. More preferably, a size of the siRNA may be 19 to 25 nucleotides.

The siRNA sequence may be designed by using the siRNA design computer program available from the Ambion website (http://www.ambion.com/techlib/misc/siRNA_finder.html).

The siRNA may be modified as appropriate. For example, cholesterol-conjugated siRNA has been indicated to improve pharmacological characteristics (Song at al. Nature Med. 9:34751, 2003).

Specific examples of siRNA sense strands for each target genes includes the nucleotide sequence of SEQ ID NO: 1 or 3 for SON, the nucleotide sequence of SEQ ID NO: 5 for MCM5, the nucleotide sequence of SEQ ID NO: 7 for WDR5, the nucleotide sequence of SEQ ID NO: 9 for PBK, and the nucleotide sequence of SEQ ID NO: 11 for CENPA. The antisense strands may be selected from nucleotide sequences that have substantially the same lengths as the sense strands, and that hybridize with the sense strands. More specifically, the siRNA represents the double-stranded RNAs of the following nucleotide sequences.

```
SON:
                                        (SEQ ID NO: 1)
Sense strand-1:     5'-gcaucuagacguucuaugaug-3'

(SEQ ID NO: 2)
Antisense strand-1: 5'-ucauagaacgucuagaugcua-3'

(SEQ ID NO: 3)
Sense strand-2:     5'-gauucuuacaccgauucuuac-3'

(SEQ ID NO: 4)
Antisense strand-2: 5'-aagaaucggguguaagaaucag-3'

MCM5:
                                        (SEQ ID NO: 5)
Sense strand:       5'-gaacucaagcggcauuacaac-3'

(SEQ ID NO: 6)
Antisense strand:   5'-uguaaugcogcuugaguucau-3'

WDR5:
                                        (SEQ ID NO: 7)
Sense strand:       5'-gaggccccuucagucuuguuc-3'

(SEQ ID NO: 8)
Antisense strand:   5'-acaagacugaaggggccucgc-3'

PBK:
                                        (SEQ ID NO: 9)
Sense strand:       5'-cugugauguaggagucucucu-3'

(SEQ ID NO: 10)
Antisense strand:   5'-agagacuccuacaucacagau-3'

CENPA:
                                        (SEQ ID NO: 11)
Sense strand:       5'-ggguauuuuuguaguuucuuu-3'

(SEQ ID NO: 12)
Antisense strand:   5'-agaaacuacaaaaauacccau-3'
```

The antisense strand of the siRNA of the present invention may include the nucleotide sequence of SEQ ID NOS: 2, 4, 6, 8, 10 or 12 as an antisense strand, and the sense strand may be selected from nucleotide sequences that have substantially the same lengths as the antisense strand, and that hybridize with the antisense strand. Further, as will be described in Examples below, the siRNA may be expressed by using a vector expressing a short-hairpin RNA (shRNA) (for example, pSUPER vector, Oligoengine), from which a shRNA including the 19 bases on each 5'-end of the sense strand and the antisense strand is expressed. It is known that the shRNA is processed in a cell and converted into siRNA.

The siRNA may be directly introduced into a cell in a form that can bind to the target mRNA. Alternatively, an introduction of an expression vector having incorporated a siRNA-encoding DNA into a cell also may be used. For the introduction of the vector into a cell, transfection promoters such as FuGENE (Roche diagnostices), Lipofectamine 2000 (Invitrogen), Oligofectamine (Invitrogen), and Nucleofector (Wako Pure Chemical Industries, Ltd.) may be used.

When using an expression vector, for example, the antisense strand for the target mRNA is transcribed with a first promoter (for example, the promoter sequence on the 3'-end of the cloned DNA), and the sense strand with a second promoter (for example, the promoter sequence on the 5'-end of the cloned DNA). In this case, the sense strand and the antisense strand hybridize and form a double strand in a cell. Alternatively, the siRNA sense strand and antisense strand may be separately transcribed using two vectors. The template DNA may encode a siRNA having a secondary structure, for example, such as a hairpin structure, and, in this case, a single transcript includes both the sense strand and the antisense strand. In order to form a hairpin loop structure, any loop sequence is interposed between the sense strand and the antisense strand. The loop sequence may be selected from the list in the Abion website.

The screening method of the present invention is described below.

The screening method of the present invention specifies an active ingredient of a pancreatic cancer therapeutic agent from candidate substances that lower the expression level of at least one of SON gene, MCM5 gene, WDR5 gene, PBK gene and CENPA gene, or that lower the bioactivity of the protein encoded by the gene.

Specifically, the screening method of the present invention screens for compounds or the like that inhibit gene expression or the biological activity of protein encoded by the gene, using the target gene, the protein encoded by the gene, or the transcription regulatory region of the gene.

For example, a screening method for the target protein comprises:

(1) a step of contacting a candidate substance to the target protein;

(2) detecting the binding activity of the target protein with the candidate substance; and (3) selecting a substance that binds to the target protein.

The detection of the binding activity between the target protein and the candidate substance in step (2) may be performed by using methods such as an immunoprecipitation method (for example, Harlow and Lane, Antibodies, 511-52, Cold Spring Harbor Laboratory publications, New York, 1988), the west-western blotting analysis (Skolnik et al., Cell 65: 83-90, 1991), and the two-hybrid system (Dalton and Treisman, Cell 68: 597-612, 1992, Fields and Sternglanz, Trends Genet 10: 28692, 1994). Further, screening also may be performed by using affinity chromatography, or a biosensor that uses the surface plasmon resonance phenomenon.

Further, screening also may be performed by using, for example, a method that screens for a binding substance by contacting a low-molecular compound library, a natural substance bank, or a random phage peptide display library with the immobilized target protein, or a high-throughput screening method that is based on the combinatorial chemistry technique for isolating a substance binding to the target protein (Wrighton et al., Science 273: 458-64, 1996; Verdine, Nature 384: 11-13, 1996; Hogan, Nature 384: 17-9, 1996).

For the screening of a substance that lowers the bioactivity of the target protein, the screening method includes, for example, the following steps.

(1) a step of contacting a candidate substance to the target protein;

(2) a step of detecting the biological activity of the target protein; and (3) a step of comparing the target protein biological activity with the biological activity of the target protein detected in the absence of the candidate substance, and selecting a substance that inhibits the biological activity of the target protein.

Specifically, because the target protein of the present invention has a role in the proliferation, survival and tumorigenicity of pancreatic cancer cells, a substance that inhibits these activities can be specified.

The substance specifically screened is, for example, an antagonist to the target protein.

The screening method of the present invention also screens for a substance that lowers the expression level of the target gene. The method comprises, for example, the following steps.

(1) a step of contacting a candidate substance with a cell expressing the target gene;

(2) a step of measuring the expression level of the target gene in the cell; and (3) a step of selecting a substance that lowers the expression level of the target gene more than a control.

The cell expressing the target gene may include cell lines established from pancreatic cancer cells (for example, KLM1, PK1, PK59, MIA PACa-2, etc.). It is also possible to transfect normal cells with the target gene DNA. Expression levels may be detected by using methods known in the art.

The screening method of the present invention may target a substance that acts on the transcription regulatory region of the target gene. The method comprises, for example, the following steps.

(1) a step of contacting a candidate substance with a cell to which a vector containing a fused DNA containing a reporter gene ligated downstream of the transcription regulatory region of the target gene is introduced;

(2) a step of measuring the reporter gene expression; and (3) a step of selecting a substance that lowers the reporter gene expression.

Such reporter assay is known in the art, and reporter genes and host cells may be appropriately selected.

The candidate substance used in the screening method may include cell extracts, cell culture supernatants, microorganism fermentation products, marine organism extracts, plant extracts, purified proteins or crude proteins, peptides, non-peptide compounds, synthetic low-molecular compounds, and natural compounds.

The following specifically describes the present invention in more detail based on Examples. The present invention, however, is not limited by the following Examples.

EXAMPLE 1

The effect of siRNA on the proliferation of pancreatic cancer cells was examined.

Human pancreatic cancer cell line MIA PaCa-2 was inoculated on a 96-well plate ($5 \times 10^3$ cells/well), and cultured overnight at 37° C. under 5% $CO_2$ in a Dulbecco's Modified Eagle Medium (DMEM+10% PBS) supplemented with 10% fetal bovine serum. On the next day, the siRNAs below were introduced at 10, 50 or 100 nM concentrations using oligofectamine (Invitrogen). The method detailed in the manufacturer's protocol was used for the introduction.

siRNA for SON: Sense strand-1 (SEQ ID NO: 1) and antisense strand-1 (SEQ ID NO: 2)

siRNA for MCM5: Sense strand (SEQ ID NO: 5) and antisense strand (SEQ ID NO: 6)

siRNA for WDR5: Sense strand (SEQ ID NO: 7) and antisense strand (SEQ ID NO: 8)

siRNA for PBK: Sense strand (SEQ ID NO: 9) and antisense strand(SEQ ID NO: 10)

siRNA for CENPA: Sense strand (SEQ ID NO: 11) and antisense strand (SEQ ID NO: 12)

After the introduction, the cells were cultured in DMEM+ 10% FBS for 5 days, and the extent of cell proliferation was measured daily by a calorimetric method (MTT assay) using 3-[4,5-dimethylthiazol-2-yl]-2,5-diphenyltetrazolium bromide.

The extent of proliferation on day 4 post introduction is presented in FIG. 1. The proliferation of the cells with the introduced siRNA was significantly inhibited compared to the cells to which siRNA that did not have a complementary sequence to any of the human genes was introduced (negative control).

The siRNA for SON with sense strand-2 (SEQ ID NO: 3) and antisense strand-2 (SEQ ID NO: 4) inhibited cell proliferation as effectively as the siRNA that had sense strand-1 and antisense strand-1.

These results confirmed that the siRNAs of the present invention were able to effectively inhibit the proliferation of pancreatic cancer cells.

EXAMPLE 2

Relatively long term effects of siRNA on the survival and proliferation of pancreatic cancer cells were examined by using a vector that expresses shRNA having the same sequences as the 19 bases on each 5'-end of the siRNA of SEQ ID NOS: 1 and 2, 5 and 6, 7 and 8, 9 and 10, or 11 and 12, using a pSUPER vector expressing short-hairpin RNA (shRNA). The vector was constructed according to the protocol of Oligoengine. Each shRNA expression vector was introduced into pancreatic cancer cell lines MIA PACa-2 and PCI-35 using Lipofectamine (Invitrogen), and the number of viable colonies was counted after 4 weeks of selective culturing with G418. The method detailed in the manufacturer's protocol was used for the introduction.

Figure 2:
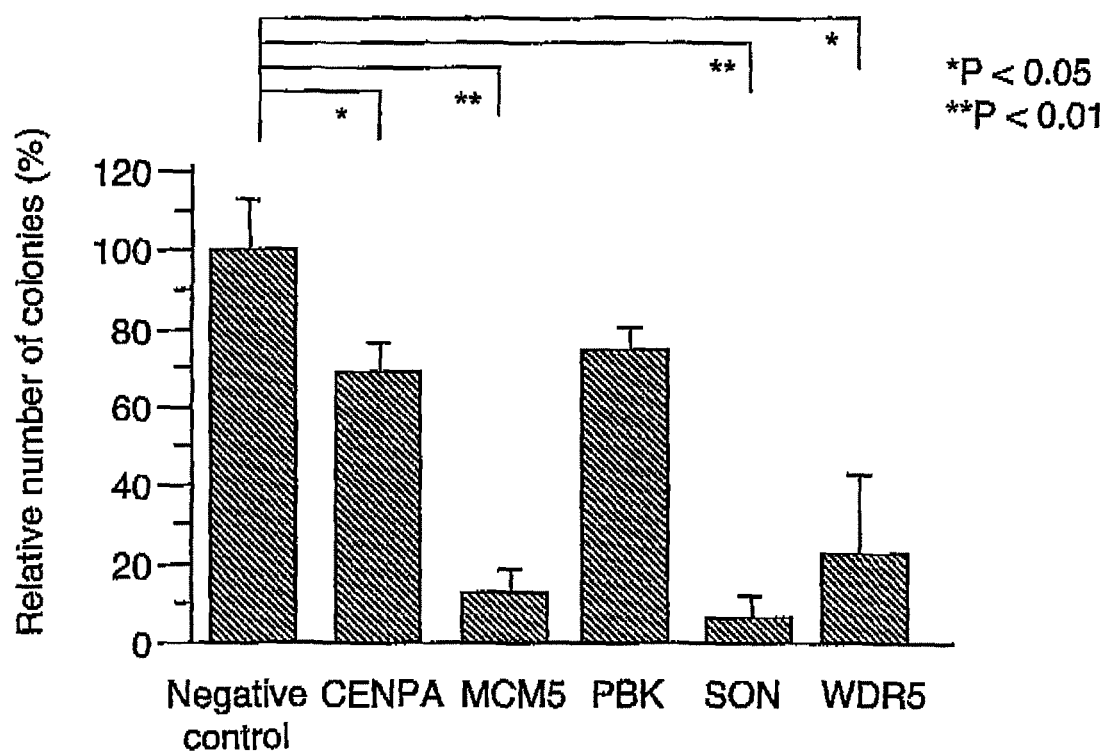
[FIG. 2] The results of examining the effect of siRNA on the survival and proliferation of pancreatic cancer cells in Example 2.

The number of viable colonies of MIA PaCa-2 cells is presented in FIG. 2. The number of viable colonies of the cells to which the shRNA expression vectors corresponding to the siRNAs of SEQ ID NOS: 1-2, 5-6, 7-8, 9-10, or 11-12 was introduced was significantly inhibited compared to the cells to which the shRNA expression vector corresponding to the negative control siRNA was introduced.

These results confirmed that the siRNAs of the present invention were able to effectively inhibit the survival of pancreatic cancer cells.

EXAMPLE 3

The effect of siRNA on the tumorigenicity of pancreatic cancer cells was examined with a shRNA constitutive expression clone established by selecting MIA PACa-2cells in a G418 selective medium after a shRNA expression vector containing the same sequences as the 19 bases at each 5'-end of the siRNAs of SEQ ID NOS: 1 and 2, 7 and 8, 9 and 10, or 11 and 12 was introduced into the MIA PACa-2 cells. The clone was subcutaneously transplanted into a nude mouse, and the mouse was observed for 6 weeks for any resulting tumor size.

Figure 3:
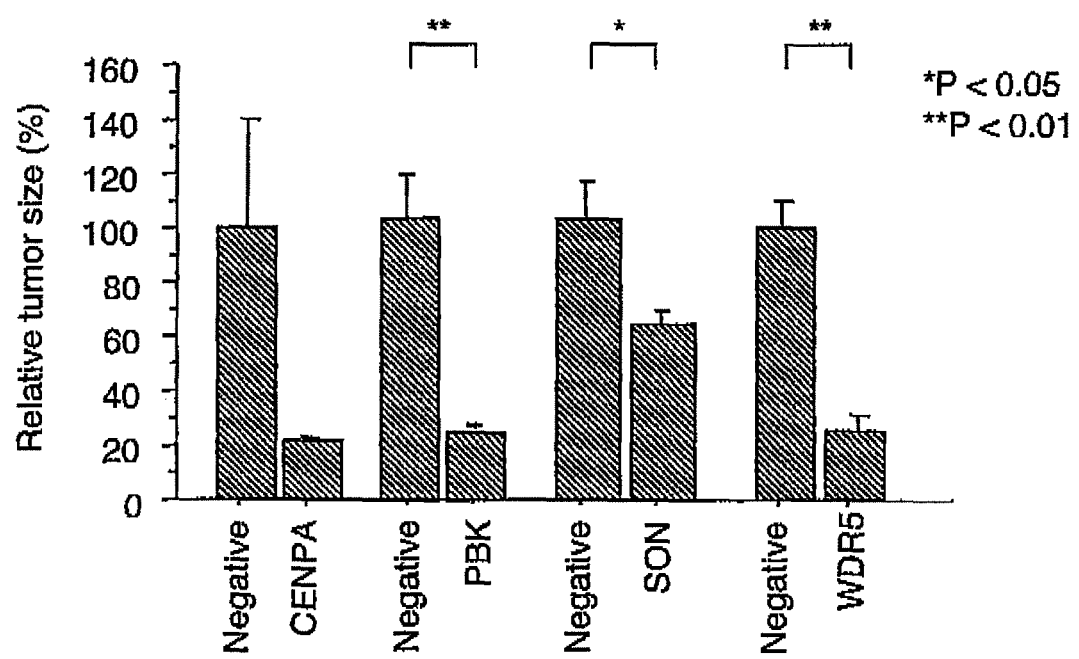
[FIG. 3] The results of examining the effect of siRNA on the tumorigenicity of pancreatic cancer cells in Example 3.

The results are presented in FIG. 3. The tumorigenicity of the cells to which the shRNA expression vectors were introduced was significantly inhibited compared to the shRNA expression clone corresponding to the negative control siRNA.

These results confirmed that the siRNAs of the present invention were able to effectively inhibit the tumorigenicity of pancreatic cancer cells. It should be noted that the effect of the siRNA of SEQ ID NOS: 5 and 6 on the tumorigenicity of pancreatic cancer cells remains unknown, because clones that constitutively expressed the shRNA containing the siRNA sequence targeting the MCM5 of SEQ ID NO: 5 and 6 were not obtained.

EXAMPLE 4

The effect of siRNA on the proliferation of normal pancreatic ductal epithelial cells and pancreatic cancer cells was examined.

Each siRNA was introduced into normal pancreatic ductal epithelial cells (HPDE) and pancreatic cancer cell line (MIA PACa-2) using the method of Example 1, and the extent of cell proliferation was measured according to the method used in Example 1.

Figure 4:
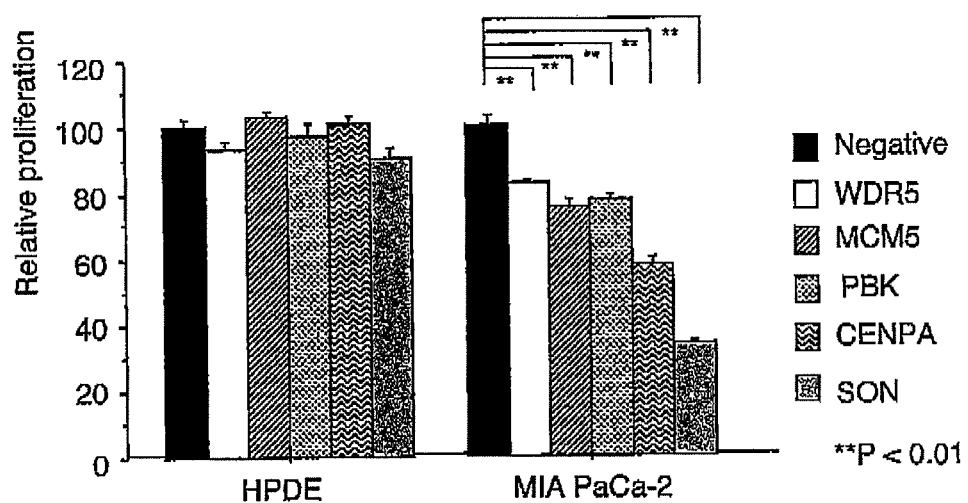
[FIG. 4] The results of examining the effect of siRNA on the proliferation of each of normal pancreatic ductal epithelial cells and pancreatic cancer cells in Example 4.

The results are presented in FIG. 4. The siRNAs did not have significant effects for inhibiting the proliferation of the normal cells.

The invention claimed is:

1. A method for treating pancreatic cancer, which comprises administering to a patient with pancreatic cancer a composition that comprises a pharmaceutically effective amount of an antisense nucleic acid or siRNA which inhibits expression of a SON gene.

2. The method of claim 1, wherein a sense strand of the siRNA inhibiting expression of the SON gene comprises SEQ ID NO: 1 or SEQ ID NO: 3.

* * * * *

SEQUENCE LISTING

```
<160> NUMBER OF SEQ ID NOS: 12

<210> SEQ ID NO 1
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1
gcaucuagac guucuaugau g                                                   21

<210> SEQ ID NO 2
<211> LENGTH: 21
<212> TYPE: RNA
<213> ORGANISM: Artificial Sequence
<220> FEATURE:
<223> OTHER INFORMATION: Synthetic Construct

<400> SEQUENCE: 2
ucauagaacg ucuagaugcu a                                                   21

<210> SEQ ID NO 3
<211> LENGTH: 21
<212> TYPE: RNA
<213> ORGANISM: Artificial Sequence
<220> FEATURE:
<223> OTHER INFORMATION: Synthetic Construct

<400> SEQUENCE: 3
gauucuuaca ccgauucuua c                                                   21

<210> SEQ ID NO 4
<211> LENGTH: 21
<212> TYPE: RNA
<213> ORGANISM: Artificial Sequence
<220> FEATURE:
<223> OTHER INFORMATION: Synthetic Construct

<400> SEQUENCE: 4
aagaaucggu guaagaauca g                                                   21

<210> SEQ ID NO 5
<211> LENGTH: 21
<212> TYPE: RNA
<213> ORGANISM: Artificial Sequence
<220> FEATURE:
<223> OTHER INFORMATION: Synthetic Construct

<400> SEQUENCE: 5
gaacucaagc ggcauuacaa c                                                   21
```

<210> SEQ ID NO 6
<211> LENGTH: 21
<212> TYPE: RNA
<213> ORGANISM: Artificial Sequence
<220> FEATURE:
<223> OTHER INFORMATION: Synthetic Construct

<400> SEQUENCE: 6
uguaaugccg cuugaguuca u                                              21

<210> SEQ ID NO 7
<211> LENGTH: 21
<212> TYPE: RNA
<213> ORGANISM: Artificial Sequence
<220> FEATURE:
<223> OTHER INFORMATION: Synthetic Construct

<400> SEQUENCE: 7
gaggccccuu cagucuuguu c                                              21

<210> SEQ ID NO 8
<211> LENGTH: 21
<212> TYPE: RNA
<213> ORGANISM: Artificial Sequence
<220> FEATURE:
<223> OTHER INFORMATION: Synthetic Construct

<400> SEQUENCE: 8
acaagacuga aggggccucg c                                              21

<210> SEQ ID NO 9
<211> LENGTH: 21
<212> TYPE: RNA
<213> ORGANISM: Artificial Sequence
<220> FEATURE:
<223> OTHER INFORMATION: Synthetic Construct

<400> SEQUENCE: 9
cugugaugua ggagucucuc u                                              21

<210> SEQ ID NO 10
<211> LENGTH: 21
<212> TYPE: RNA
<213> ORGANISM: Artificial Sequence
<220> FEATURE:
<223> OTHER INFORMATION: Synthetic Construct

<400> SEQUENCE: 10
agagacuccu acaucacaga u                                              21

<210> SEQ ID NO 11
<211> LENGTH: 21
<212> TYPE: RNA
<213> ORGANISM: Artificial Sequence
<220> FEATURE:
<223> OTHER INFORMATION: Synthetic Construct

<400> SEQUENCE: 11
ggguauuuuu guaguuucuu u                                              21

<210> SEQ ID NO 12
<211> LENGTH: 21
<212> TYPE: RNA
<213> ORGANISM: Artificial Sequence
<220> FEATURE:
<223> OTHER INFORMATION: Synthetic Construct

```
<400> SEQUENCE: 12
agaaacuaca aaaauaccca u                                              21
```